United States Patent
Liu

(12) 
(10) Patent No.: US 6,417,166 B2
(45) Date of Patent: *Jul. 9, 2002

(54) THIN MINERALIZED COLLAGEN MEMBRANE AND METHOD OF MAKING SAME

(75) Inventor: Sung-Tsuen Liu, Laguna Niguel, CA (US)

(73) Assignee: Ceramedical, Inc., Laguna Niguel, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/861,113

(22) Filed: May 19, 2001

Related U.S. Application Data

(63) Continuation-in-part of application No. 09/385,238, filed on Aug. 28, 1999.
(51) Int. Cl.$^7$ ............................................... A61K 38/01
(52) U.S. Cl. ........................... 514/21; 514/2; 424/543; 424/549; 424/682; 424/686; 424/687
(58) Field of Search ................................ 424/543, 548, 424/572; 514/2, 21

(56) References Cited

U.S. PATENT DOCUMENTS

| | | | |
|---|---|---|---|
| 5,231,169 A | | 7/1993 | Constantz |
| 5,320,844 A | | 6/1994 | Sung-Tsuen |
| 5,425,770 A | * | 6/1995 | Piez et al. ............... 623/16 |
| 5,455,231 A | | 10/1995 | Constantz |
| 5,532,217 A | * | 7/1996 | Silver et al. ............... 514/21 |

FOREIGN PATENT DOCUMENTS

| DE | 19812713 | 9/1999 |
|---|---|---|

OTHER PUBLICATIONS

Bioceramics of Calcium Phosphate, Klaus de Groot, PhD. CRC Press, Boca Raton, Fla, 1983, pp. 1–32.

Absorbable Collagen Membrane for Guided Tissue Regeneraticuin Dental Surgery, Sulzer Calcitek, Inc Date Unknown pp. 1–6.

Guidor, The Bioresorbuble Matrix Barrier John, O. Butler, Co. pp. 2, 4 Date Unknown.

* cited by examiner

*Primary Examiner*—Jean C. Witz
(74) *Attorney, Agent, or Firm*—Howard R. Lambert

(57) ABSTRACT

A strong, thin flexible mineralized collagen membrane is disclosed that is useful for such medical applications as a barrier for guided tissue regeneration, periodontal defect repair, bone grafts and skin wound repair. The mineralized collagen membrane comprises a substantially homogeneous mineralized collagen composite consisting essentially of about 30% to about 70% by weight of a collagen component and about 30% to about 70% by weight of a calcium phosphate minerals component precipitated from a collagen slurry by a soluble calcium ion-containing solution and a soluble phosphate ion-containing solution. The calcium phosphate minerals component has a mole ratio of calcium to phosphate in the range of about 1.0 to about 2.0. The thin mineralized collagen membrane has a bulk density of the membrane of at least about 1.0 g/cm$^3$ and has a thickness not greater than about 0.5 mm and preferably not greater than about 0.3 mm. A corresponding method of making the mineralized collagen membrane includes casting washed mineralized collagen slurry as a thin, flat sheet onto a surface, such as a sieve or filter paper, air drying the sheet and removing it from the surface as the thin mineralized collagen membrane.

33 Claims, No Drawings

THIN MINERALIZED COLLAGEN MEMBRANE AND METHOD OF MAKING SAME

This application is a Continuation-in part (CIP) of application Ser. No. 09/385,238, filed Aug. 28, 1999.

BACKGROUND OF THE INVENTION

1. Field of the Invention

The present invention relates generally to the field of mineralized collagen materials and methods of producing the same and more particularly to thin mineralized collagen structures useful for medical applications, such as guided tissue regeneration (GTR) procedures, and methods for producing the thin mineralized collagen structures.

2. Background Discussion

By way of definition, collagen is an inert natural protein found in human and animal skin, connective tissue, bones and teeth; apatite is a calcium phosphate mineral and is the most important mineral constituent of bones and teeth. With respect to the latter, bone typically contains sixty to seventy-five percent by weight of biological apatite and teeth typically contain more than ninety-eight percent by weight of biological apatite. Biological apatite has a crystal structure similar to that of pure hydroxyapatite, but contains some substitute ions for calcium, phosphate, and hydroxyl ions. Strictly speaking, synthetically produced, precipitated hydroxyapatite is more similar to biological apatite than are the hydroxyapatite ceramics.

It is already known that collagen can be mineralized by calcium phosphate minerals by inducing the precipitation of calcium phosphate in a collagen slurry. Several patents have disclosed the methods of preparation mineralized collagen by this precipitation of calcium phosphate.

As an example, my prior U.S. Pat. No. 5,320,844 discloses a mineralized collagen composite material produced by quickly adding a soluble calcium ion-containing solution and a phosphate ion-containing solution into a collagen slurry. The patent further discloses that the slurry is to be vigorously stirred while maintaining it at a pH of 7 or higher to thereby induce the mineralization of the collagen. The mineralized collagen is disclosed as being recovered by solid-liquid separation and by then being dried. However, my prior patent does not disclose a thin mineralized collagen membrane or how such a membrane might be made.

In addition, U.S. Pat. No. 5,455,231 and 5,231,169 and foreign patent WO 93/12736 to Brent R. Constantz et al. describe methods of mineralizing collagen by dispersing collagen in an alkaline solution and subsequently mixing soluble calcium and phosphate containing solutions to the collagen for over an hour while maintaining the resulting collagen slurry at a pH of 10 or higher.

The present inventor has observed that mineralized collagen exhibits very different physical and mechanical properties than those of pure collagen. For example, membranes made from collagen only are weak in mechanical strength. Such collagen-only membranes show swelling when soaked in water, are difficult and slippery to handle, do not have the conductivity property needed for bone growth and their resorption rate is difficult to control.

In contrast, mineralized collagen is considered by the present inventor to provide better biocompatibility toward animal and human tissue than does pure collagen. As hard tissue implant material, mineralized collagen also has a conductivity effect that enhances hard tissue (e.g., bone) growth. Moreover, mineralized collagen has properties that are significantly different from simple collagen-calcium phosphate mixtures, for example, as disclosed in U.S. Pat. No. 5,425,770 to Karl A. Piez et al It is often necessary or desired to regenerate injured or defective animal or human tissue, including hard tissue such as bone. In order to assist such tissue generation, a so-called guided tissue regeneration (GTR) barrier material is typically applied to the tissue region to be regenerated So far as is known to the present inventor, mineralized collagen has heretofore been prepared by freeze-drying to form a sponge structure or is alternatively prepared in solid block or granule form. However, none of these mineralized forms of collagen can be used as membrane barriers for GTR procedures, and no strong, mineralized collagen thin membranes that would be suitable for GTR applications are believed by the present inventor to have been used or disclosed For more than a decade, thin polytetrafluoroethylene (PTFE) membranes have been used as barriers for GTR procedures in repairing periodontal defects. However, such known PTFE membrane barriers are non-resorbable. The use of such non-resorbable PTFE membranes for GTR procedures requires a two step tissue regeneration procedure. For example, in a first periodontal tissue regeneration step, the non-resorbable barrier material is inserted into or onto the periodontal defect. In a second step, after an initial healing period of about four to six weeks, the barrier material is surgically removed. This two step procedure associated with the use of a non-resorbable GTR barrier material is relatively costly, and the second, surgical-removal step increases the risk of patient infection and of other undesirable side effects.

In an attempt to simplify and reduce the cost of GTR procedures, thin, resorbable polymer membranes have recently been developed and tested in GTR applications. So far as is known to the present inventor, such resorbable polymers comprise either polylactic acid blended with a citric acid ester or a copolymer made of glycolide and lactide polymers. These polymers degrade directly to acid during the resorption process.

Examples of such resorbable polymer membranes are the GUIDOR product available from the John 0. Butler Company and the CORE RESOLUTE XT product available from W. L. Core Associates.

However, medical devices made from the above types of resorbable polymer membranes have been associated with an inflammatory response, which may be caused by the accumulation of the acid of the degradation product.

More recently, membranes made from non-mineralized collagen (for example, BIOMED material available from Sulzer Medica) have been used in GTR applications for periodontal defect repair. However, membranes made from non-mineralized collagen is normally weak in strength and is therefore difficult to manipulate. Furthermore, the resorption rate of such non-mineralized membranes is difficult to match with the normal tissue-healing process.

It is, therefore, a principle objective of the present invention to provide a strong, thin, flexible mineralized collagen membrane that is biocompatable with human tissue, that is resorbable in GTR applications and which has a controllable resorption rate. It is also an objective to provide a method for making such a mineralized collagen membrane.

Such a mineralized collagen membrane would eliminate the above-mentioned second step of surgically removing the GTR barrier and would thereby simplify and reduce the cost of the GTR procedures for both soft tissue and hard tissue repair.

SUMMARY OF THE INVENTION

In accordance with the present invention a strong, thin flexible mineralized collagen membrane useful for medical applications comprises a substantially homogeneous mineralized collagen composite. The composite consists essentially of between about 30% and about 70% by weight of a collagen component and between about 30% and about 70% by weight of a calcium phosphate minerals component precipitated from a collagen slurry by a soluble calcium ion-containing solution and a soluble phosphate ion-containing solution. The collagen component may include natural collagen and recombinant collagen. The thin mineralized collagen membrane has a thickness that is preferably not greater than about 0.5 mm and a thickness that is more preferably not greater than about 0.3 mm.

The mineralized collagen membrane useful for medical applications preferably comprises a substantially homogeneous mineralized collagen composite of between about 30% to about 70% by weight of a collagen component and between about 30% and about 70% by weight of calcium phosphate minerals. The calcium phosphate minerals component is preferably selected from the group consisting essentially of calcium phosphate, tri-calcium phosphate, octa-calcium phosphate, calcium deficient apatite, amorphous calcium phosphate, hydroxyapatite, substitute apatite, apatite-like minerals, and mixture thereof. Preferably the calcium phosphate minerals component has a mole ratio of calcium to phosphate in the range of about 1.0 to about 2.0; more preferably, the mole ratio of calcium to phosphate of about 1.67. Preferably, the mineralized collagen membrane will have a bulk density of about 1.0 g/cm$^3$ or higher.

A method of making or producing a substantially homogeneous thin mineralized collagen membrane comprises the steps of forming a collagen slurry, forming a soluble calcium ion-containing solution, forming a soluble phosphate ion containing solution, and adding the soluble calcium ion-containing solution and the soluble phosphate ion-containing solution to the collagen slurry while stirring, preferably vigorously stirring, the collagen slurry and maintaining the pH of said collagen slurry at least about 7, thereby inducing the precipitation of calcium phosphate mineral in the collagen slurry as mineralized collagen slurry.

The method includes the further steps of recovering the mineralized collagen slurry by solid-liquid separation, washing the recovered mineralized collagen slurry with pure water, casting the washed mineralized collagen slurry into a thin flat sheet, and drying the thin flat sheet to form a thin mineralized collagen membrane. The washed mineralized collagen slurry may be cast into a thin sheet on a filter media, after which the thin sheet is dried, preferably air dried, and is then removed from the filter media as a thin mineralized collagen membrane. In either case, the thin mineralized collagen membrane has a preferred thickness not greater than about 0.5 mm and a more preferably thickness not greater than about 0.3 mm.

The step of adding the soluble calcium ion-containing solution and the soluble phosphate ion-containing solution to the collagen slurry includes adding the soluble calcium ion-containing solution and the soluble phosphate ion-containing solution to the collagen either simultaneously or separately at different times, and preferably includes maintaining the collagen slurry at a pH of at least about 7.

Preferably, the steps of forming a soluble calcium ion-containing solution and a soluble phosphate ion-containing solution includes forming these solutions so that the mineralized collagen membrane comprises between about 30% and about 70% by weight of calcium phosphate minerals and between about 30% and about 70% by weight of collagen. The soluble calcium ion-containing solution and the soluble phosphate ion-containing solution are formed so that the calcium phosphate minerals comprise calcium phosphate, tri-calcium phosphate, octa-calcium phosphate, calcium deficient apatite, amorphous calcium phosphate, hydroxyapatite, substitute apatite, apatite-like minerals, or a mixture thereof.

It is preferred that the method for producing a substantially homogeneous mineralized collagen includes the step of aging the collagen slurry sufficiently long after the step of adding the soluble calcium ion-containing solution and the soluble phosphate ion-containing solution to the collagen slurry to ensure the near complete precipitation of calcium phosphate. Preferably, the pH of the slurry is maintained at between about 7 and about 9 or higher, with the higher pH being preferred.

A drug or a combination of drugs may be incorporated into the mineralized collagen membrane by adding the drug or drugs into the purified mineralized collagen slurry before processing the material into a thin membrane. Alternatively, the drug or drugs may be incorporated by soaking the thin mineralized collagen membrane into soluble drug solution and then drying the thin membrane. The drug or drugs may include antibiotics, bone morphogenetic proteins, other bone growth factors, skin growth factors, antiscarring agents and/or combinations thereof.

The method may adding a cross-linking reagent into the mineralized collagen slurry before the slurry is formed into a thin sheet. Alternatively, the dry mineralized collagen membrane may be soaked in a collagen cross-linking reagent, in which case, after the cross-linking process is completed, the membrane is soaked and washed with pure water to remove any un-reacted cross-linking reagent.

The strong, thin flexible mineralized collagen membrane of the present invention provides mechanical properties superior to those of pure collagen membranes and has important medical applications, such as use for a barrier for tissue regeneration procedures, periodontal repair and wound healing.

DESCRIPTION OF THE PREFERRED EMBODIMENT

The present inventor has determined that the use of thin, mineralized collagen membranes of the present invention is particularly advantageous for use as a barrier for GTR procedure because the membranes will be reabsorbed during the tissue healing interval such that the above-mentioned, previous second step of surgically removing the barrier is eliminated.

For preparation of the mineralized collagen membrane of the present invention, any suitable collagen component, including natural collagen or recombinant collagen, may be used. The natural collagen sources may come from skin, tendon or bone of animals such as bovine, porcine, equine, chicken or the like. The preferred starting collagen materials is non-mineralized collagen. The initial collagen material can be any solid form, solution or slurry.

The initial step in the preparation of the membrane form mineralized collagen is the preparation of a collagen slurry. If solid collagen is used, it is preferably dispersed in an acidic or alkaline solution to form a homogeneous gel-type slurry. The concentration of the collagen slurry suitable for following mineralization process is preferably between about 0.1 percent and about 5.0 percent.

In general, either a soluble calcium ion-containing component (for example, a calcium salt) or a soluble phosphate ion-containing component (for example, a phosphate salt) is then dissolved or otherwise directly combined into the collagen slurry.

If a calcium ion-containing component is directly combined into the collagen slurry, the second, phosphate ion-containing component is preferably separately dissolved or otherwise combined in a liquid medium, preferably water, to form a solution. Alternatively, if a phosphate ion-containing component is directly combined into the collagen slurry, the second, calcium ion-containing component is preferably separately dissolved or otherwise combined in a liquid medium, preferably water, to form a solution. In either such case, the second (phosphate ion-containing or calcium ion-containing) component is preferably quickly added (for example, by pouring) into the collagen slurry.

Alternately, two separate solutions, one with a soluble calcium ion-containing component and the other with a phosphate ion-containing component, can be prepared, and the two solutions are preferably quickly and simultaneously added (poured) into the collagen slurry, or the two solutions may be added to the collagen slurry slowly. Preferably, but not necessarily, stoichiometric amounts of calcium and phosphate ions are added to the collagen slurry.

In either case, during the combination step, the collagen slurry is vigorously mixed or stirred to ensure the formation of homogeneous slurry reaction product. Although, the rapidity of adding the calcium ion-containing component or phosphate ion-containing component, or both, to the collagen slurry is not critical the addition is preferably quickly performed to assure a homogeneous reaction product.

After the complete addition of the calcium ion-containing and phosphate ion-containing components to the collagen slurry, the slurry is either continuously stirred or allowed to stand un-stirred until the calcium phosphate reaction product has completely precipitated.

During the preparation procedure, the temperature of the mixture is preferably maintained below about 40° C. Moreover, during the precipitation of calcium phosphate the collagen slurry is preferably maintained at a pH value of at least about 7.0 and more preferably at a pH value of at least about 9. This pH control can be achieved by adding enough alkaline solution, such as sodium hydroxide, potassium hydroxide or ammonium hydroxide, to either the collagen slurry or the phosphate ion-containing solution before its combining with the slurry.

A calcium phosphate saturated solution at a pH value near 8 or higher will normally induce the precipitation of hydroxyapatite, substitute apatite or calcium apatite-like calcium phosphate minerals.

Other components may also be incorporated into the calcium phosphate mineral. For example, if carbonate apatite or fluoride apatite is to be incorporated into the mineralized collagen product, a soluble carbonate or soluble fluoride salt can be added into the phosphate ion-containing solution before its addition to the collagen slurry.

After the calcium phosphate mineral is completely precipitated, the resulting mineralized collagen slurry is separated and purified, for example, by being filtered and/or centrifuged and/or washed several times until the material is free of other soluble components, such as entrapped soluble impurities.

The purified mineralized collagen is then re-slurried with sufficient water to form a homogeneous slurry. This homogeneous mineralized collagen slurry is then filtered or cast into a thin flat sheet and air dried to form a thin mineralized collagen membrane. In this regard, the preferred procedure is to de-water the diluted mineralized collagen slurry by sieving the slurry using a flat-type of mesh sieve with mesh number of about or higher. The thin wet slurry sheet that remains on the sieve is then dried—preferably, air dried—to form a thin mineralized collagen membrane that is strong and flexible, and still retains its flat shape and original size after drying and removal from the sieve. Alternatively, the mineralized collagen slurry may be cast as a thin sheet onto any appropriate clean surface. The thin wet slurry sheet on the surface is then dried—preferably, air dried—to form the thin mineralized collagen membrane.

Preferably the dry thin mineralized collagen membrane formed as described a has a thickness no greater than about 0.5 mm and still more preferably has a thickness no greater than about 0.3 mm.

The calcium phosphate mineral deposited in the collagen slurry at a slurry pH value near neutral or up to about 8 is most likely calcium phosphate, tri-calcium phosphate, octa-calcium phosphate (OCP), amorphous calcium phosphate (ACP), hydroxyapatite, calcium deficient apatite (CDA), substitute apatite (such as carbonate apatite and fluro-apatite), apatite-like minerals, or mixtures thereof.

At a slurry pH of about 8 or higher, the most probable precipitation product is hydroxyapatite or calcium apatite-like minerals. In order to induce the precipitation of a calcium apatite-like material in the collagen slurry, the preferred mole ratio of calcium to phosphate is about 1 to about 2, and is more preferably about 1.67. However, other mole ratios can also be used.

The calcium phosphate mineralized collagen membrane produced in the manner set forth above may be either crosslinked or non-crosslinked and may have widely varying compositions and still be useful for such medical applications as a barrier for GTR applications. The present inventor has however unexpectedly determined that such mineralized collagen membranes optimally comprise about 30 percent to about 70 percent by weight of collagen and about 30 percent to about 70 percent by weight of calcium phosphate containing minerals.

The calcium and phosphate containing minerals included in the mineralized collagen membrane of the present invention are preferably selected from calcium phosphates, calcium apatites (including calcium-deficient apatite, hydroxyapatite, calcium fluro-apatite, calcium carbonate apatite, and the like apatite-type minerals) and mixtures thereof.

Mineralized collagen membranes including calcium fluro-apatite can be produced by including fluoride (fluoride ion) in the phosphate containing solution or collagen slurry before the mineralization reaction take place.

The present mineralized collagen membrane may include one or more additional components useful to provide one or more desired properties to the composite membrane. Metals, such as alkali metals, other alkaline earth metals and the like, may replace at least a portion, for example, a minor portion, of the calcium. At least a portion, for example, a minor portion, of the phosphate and/or hydroxyl content of the calcium ion-containing and phosphate ion-containing minerals may be replaced by a halogen, such as a chloride or a fluoride, a carbonate and the like. The precipitated calcium ion-containing and phosphate ion-containing minerals can have a chemical composition which resembles or even simulates that of biological apatite.

As is evident from the foregoing description, different components may be added to collagen slurry, soluble calcium ion-containing solution and/or phosphate ion-containing solution used to make the present composite membrane to adjust the chemical composition of the resulting mineralized collagen membrane as may be desired.

Any suitable, preferably soluble and more preferably water soluble, calcium ion-containing component may be employed in the present methods of making mineralized collagen composite membranes, provided that such calcium ion-containing components function as described herein and result in a useful calcium phosphate mineralized collagen membrane. Calcium ion-containing salts and mixtures thereof are particularly useful. Example of calcium ion-containing salts includes calcium acetate, calcium chloride, calcium nitrate, calcium carboxylate, other soluble calcium organic salts and mixtures thereof.

Any suitable, preferably soluble and more preferably water soluble, phosphate ion-containing component may be employed in the present methods for making calcium phosphate mineralized collagen membranes, provide that such phosphate ion-containing components function as described herein and result in a useful calcium phosphate mineralized collagen membrane. Phosphate ion-containing salts and mixtures thereof are particularly useful. Examples of phosphate ion-containing salts include alkali metal phosphate salts, ammonium phosphate salts and mixture thereof.

Although any suitable liquid medium may be employed (for example, for the slurry, and/or the described solution or the solutions), the use of an aqueous liquid media is much preferred.

Various different materials may be employed to maintain or adjust the pH of the collagen slurry, the preparation of a calcium ion-containing solution and a phosphate ion-containing solution. Example of useful pH adjusting agents includes alkaline metal hydroxide, ammonium hydroxide and mixtures thereof.

Furthermore, the mineralized collagen membranes of the present invention can also incorporate drugs such as antibiotics, bone morphogenetic proteins, other bone growth factors, skin growth factors or anti-scarring agents such as transforming growth factor-Beta. In such case, the drugs will be preferably added to the mineralized collagen slurry before its processing into the mineralized collagen membrane form.

In order to enhance the mechanical strength of the mineralized collagen membranes, a collagen cross-linking reagent can be added into the mineralized collagen slurry after the precipitation and before the purification steps described above. As an alternative, the dry mineralized collagen membrane may be soaked in the collagen cross-linking reagent. After the cross-linking process is completed, the membrane is then soaked and washed with pure water to remove any un-reacted cross-linking reagent.

In addition or alternatively, drugs, such as antibiotics, bone morphogenetic proteins, other bone growth factors, skin growth factors, antiscarring agents and mixtures thereof may be added to the purified mineralized collagen slurry before processing it into membrane form. Alternately, the drug may be incorporated into the mineralized collagen membrane by soaking the membrane in a drug solution and drying the resulting drug-containing mineralized collagen membrane.

The present mineralized collagen membrane contains calcium phosphate minerals which are incorporated into the structure of collagen fibrils, the membrane being substantially homogeneous, preferably with little or no phase separation visually apparent.

Moreover, the present mineralized collagen membrane has substantial compositional flexibility and the weight ratio of precipitated calcium phosphate minerals to collagen component can be varied over a relatively wide range. By so doing, the mechanical strength and/or bioresoption rate of the present mineralized collagen membrane can be varied over a relatively wide range.

It is apparent that the present membrane is quite different from a pure collagen membrane. Pure collagen membranes without cross-linking are very weak when soaked in water and show high degrees of swelling. Furthermore, pure collagen membranes are difficult to handle and the bioresorption rate is difficult to control.

Surprisingly, the mineralized collagen membrane of the present invention has strong mechanical strength even without the described collagen cross-linking. When the present membrane is soaked in water, it does not visibly swell and retains its integrity even after months of aging in an aqueous environment.

Further, the bioresorption rate of my new mineralized collagen membrane can be controlled by changing the content of calcium phosphate minerals. Still further, this mineralized collagen membrane has both excellent biocompatibility and conductivity effects for bone growth.

My new mineralized collagen membrane is considered to have many medical applications because of its flexibility, strong mechanical strength, easy manipulation character, excellent biocompability and controllable bioresorption rate. Such medical applications include membrane barriers for GTR applications for repairing periodontal defects, membranes for covering bone defect surgery and for bone substitutes, skin wound repair and healing, skin sealing, and as a carrier for antibiotic, bone growth factors, skin growth factors, and so forth.

EXAMPLE 1

1.0 gram (g) of solid fibril collagen (type 1 collaen) is added into 200 milliliters (ml) of water. 0.3 ml glacial acetic acid is then added to this aqueous mixture which is then stirred (mixed) in a blender. At this stage the collagen is in the form of a homogeneous gel slurry.

2.2 g of $CaCl_2.2H_2O$ is dissolved in 30 ml of pure water to form a calcium chloride solution, and 2.0 g of $(NH_4)2HPO_4$ is dissolved in a 30 ml of pure water to form an ammonium phosphate solution.

The pHs of the collagen slurry, the calcium chloride solution and the ammonium phosphate solution are separately adjusted to a value of about 9 by adding ammonium hydroxide before mixing together in the blender.

The collagen slurry is kept in the blender and stirred vigorously. Both the calcium chloride solution and the ammonium phosphate solution are poured simultaneously into the collagen slurry. The stirring is continued for several more minutes and then kept unstirred for about 1 hour. The resulting mineralized collagen slurry is then filtered with a 18.5 cm diameter filter paper, and is washed several times with pure water.

The filtered mineralized collagen is reslurried with water and is then homogeneously spread on the filter paper and is allowed to air dry to form a thin mineralized collagen membrane sheet. After air drying, the mineralized collagen membrane sheet is then separated from the filtration paper. The thin mineralized collagen membrane thus formed has 40% by weight of collagen and 60% by weight of calcium phosphate, and is strong and flexible.

The dried mineralized collagen membrane is visually examined and does not show separate phases of collagen and calcium phosphate.

EXAMPLE 2

1 g of collagen sheet is dispersed in 200 ml of pure water in a blender, and 0.6 g of solid NaOH is added and the mixture is stirred for several minutes to form a collagen slurry.

2.2 g $CaCl_2 \cdot 2H_2O$ is dissolved in 50 ml of pure water in a 100 ml beaker.

2.5 g $(NH_4)_2HPO_4$ is separately dissolved in 50 ml of pure water in another 100 ml beaker.

While the collagen slurry is stirred vigorously, both aqueous solutions of calcium chloride and ammonium phosphate are simultaneously poured quickly into the collagen slurry. The resulting mixture (slurry) is then continued to be stirred in the blender for several more minutes.

After allowing the slurry to stand still for about one half-hour, the slurry is then cast into a 20 cm diameter, mesh metal sieve and is washed with pure water several times. The slurry is then spread homogeneously on the top of the sieve and is air-dried to form a thin mineralized collagen membrane. After air drying, the mineralized collagen membrane is strong and flexible and weighs 2.45 g, with a composition that is 40% by weight of collagen and 60% by weight of calcium phosphate. The thin mineralized collagen membrane has a surface area of 314 $cm^2$ and has unit weight of 0.0073 $g/cm^2$ and thickness of 0.0625 mm. The apparent bulk density of the membrane is higher than about 1.1 $g/cm^3$.

EXAMPLE 3

This EXAMPLE 3 is similar to EXAMPLE 2 set forth above, except that 2 g of collagen sheet, 4.4 g of $CaCl_2 \cdot 2H_2O$ and 5.5 g $(NH_4)_2HPO_4$ are used. The thin dried mineralized collagen membrane has the same surface area as in EXAMPLE 2, but has a unit weight of 0.015 $g/cm^2$ and thickness of 0.125 mm. No separate phases of collagen and calcium phosphate are observed. After being soaked in water for several weeks, this particular mineralized collagen membrane still retains its integrity and shows no detectable swelling.

As above stated, the present inventor has determined that thin mineralized collagen membranes having thicknesses greater than those disclosed in the foregoing specific EXAMPLES are useful for medical applications.

Although there has been described above thin mineralized collagen membranes and methods for making the membranes in accordance with the present invention for purposes of illustrating the manner in which the present invention maybe used to advantage, it is to be understood that the invention is not limited thereto. Consequently, any and all variations and/or equivalent methods which may occur to those skilled in the applicable art are to be considered to be within the scope and spirit of the invention as set forth in the claims which are appended hereto as part of this application.

What is claimed is:

1. A thin mineralized collagen membrane useful for medical applications comprises a substantially homogeneous mineralized collagen composite consisting essentially of about 30% to about 70% by weight of a collagen component and about 30% to about 70% by weight of a calcium phosphate minerals component precipitated from a collagen slurry by a soluble calcium ion-containing solution and a soluble phosphate ion-containing solution, said thin mineralized collagen membrane having a thickness not greater than about 0.5 mm.

2. The thin mineralized collagen membrane as claimed in claim 1, wherein said collagen component is selected to include natural collagen, recombinant collagen or a mixture thereof.

3. The thin mineralized collagen membrane as claimed in claim 1, wherein said calcium phosphate minerals are selected from the group consisting of calcium phosphate, tri-calcium phosphate, octa-calcium phosphate, calcium deficient apatite, amorphous calcium phosphate, hydroxyapatite, substitute apatite, apatite-like minerals, and mixture thereof.

4. The thin mineralized collagen membrane as claimed in claim 1, wherein said calcium phosphate minerals component has a mole ratio of calcium to phosphate in the range of about 1.0 to about 2.0.

5. The thin mineralized collagen membrane as claimed in claim 1, wherein said calcium phosphate minerals component has a mole ratio of calcium to phosphate of about 1.67.

6. The thin mineralized collagen membrane as claimed in claim 1, wherein said mineralized collagen membrane is crosslinked.

7. The thin mineralized collagen membrane as claimed in claim 1, wherein said mineralized collagen membrane is non-crosslinked.

8. The thin mineralized collagen membrane as claimed in claim 1, wherein said mineralized collagen membrane includes a drug selected from the group consisting of antibiotics, bone morphogenetic proteins, other bone growth factors, skin growth factors, antiscarring agents and mixtures thereof.

9. The thin mineralized collagen membrane as claimed in claim 1, wherein said mineralized collagen membrane has a bulk density of at least about 1.0 $g/cm^3$.

10. The thin mineralized collagen membrane as claimed in claim 1, wherein said mineralized collagen membrane has a thickness no greater than about 0.3 mm.

11. A thin mineralized collagen membrane useful for medical applications comprises a substantially homogeneous mineralized collagen composite consisting essentially of about 30% to about 70% by weight of a collagen component and about 30% to about 70% by weight of a calcium phosphate minerals component selected from the group consisting of calcium phosphate, tri-calcium phosphate, octa-calcium phosphate, calcium deficient apatite, amorphous calcium phosphate, hydroxyapatite, substitute apatite, apatite like minerals, and mixture thereof, said calcium phosphate minerals having a mole ratio of calcium to phosphate in the range of about 1.0 to about 2.0, said mineralized collagen membrane having a bulk density of at least about 1.0 $g/cm^3$ and having a thickness not greater than about 0.5 mm.

12. The thin mineralized collagen membrane as claimed in claim 11, wherein said calcium phosphate minerals component has a mole ratio of calcium to phosphate of about 1.67.

13. The thin mineralized collagen membrane as claimed in claim 11, wherein said mineralized collagen membrane includes a drug selected from the group consisting of antibiotics, bone morphogenetic proteins, other bone growth factors, skin growth factors, antiscarring agents and mixtures thereof.

14. A method for producing a substantially homogeneous thin mineralized collagen membrane comprising the steps of:

a. forming a collagen slurry;
b. forming a soluble calcium ion-containing solution;
c. forming a soluble phosphate ion containing solution;
d. adding said soluble calcium ion-containing solution and said soluble phosphate ion-containing solution to said collagen slurry while stirring the collagen slurry and maintaining the pH of said collagen slurry at least about 7, thereby inducing the precipitation of calcium phosphate mineral in the collagen slurry as mineralized collagen slurry;
e. recovering said mineralized collagen slurry by solid-liquid separation;
f. washing the recovered mineralized collagen slurry with pure water;
g. casting the washed mineralized collagen slurry into a thin sheet; and
h. drying said thin sheet to form a thin mineralized collagen membrane having a thickness not greater than about 0.5 mm.

15. The method for producing a substantially homogeneous thin mineralized collagen membrane as claimed in claim 14, wherein the step of adding said soluble calcium ion-containing solution and said soluble phosphate ion-containing solution to said collagen slurry includes adding said soluble calcium ion-containing solution and said soluble phosphate ion-containing solution to said collagen separately at different times.

16. The method for producing a substantially homogeneous thin mineralized collagen membrane as claimed in claim 14, wherein the step of adding said soluble calcium ion-containing solution and said soluble phosphate ion-containing solution to said collagen slurry includes adding said soluble calcium ion-containing solution and said soluble phosphate ion-containing solution to said collagen substantially simultaneously.

17. The method for producing a substantially homogeneous thin mineralized collagen membrane as claimed in claim 14, wherein the step of adding said soluble calcium ion-containing solution and said soluble phosphate ion-containing solution to said collagen slurry includes maintaining of the collagen slurry at a pH of at least about 7.

18. The method for producing a substantially homogeneous thin mineralized collagen membrane as claimed in claim 14, wherein said soluble calcium ion-containing solution and said soluble phosphate ion-containing solution are formed so that the mineralized collagen membrane comprises about 30% to about 70% calcium phosphate minerals and about 30% to about 70% collagen.

19. The method for producing a substantially homogeneous thin mineralized collagen membrane as claimed in claim 14, wherein said soluble calcium ion-containing solution and said soluble phosphate ion containing solution are formed so that said calcium phosphate minerals comprise calcium phosphate, tri-calcium phosphate, octa-calcium phosphate, calcium deficient apatite, amorphous calcium phosphate, hydroxyapatite, substitute apatite, apatite-like minerals, or a mixture thereof.

20. The method for producing a substantially homogeneous thin mineralized collagen membrane as claimed in claim 14, including the step of aging the collagen slurry for sufficiently long after the step of adding said soluble calcium ion-containing solution and said soluble phosphate ion-containing solution to said collagen to ensure at least substantially complete precipitation of calcium phosphate.

21. The method for producing a substantially homogeneous mineralized collagen membrane as claimed in claim 14, including the step of adding a drug to the washed mineralized collagen slurry.

22. The method for producing a substantially homogeneous mineralized collagen membrane as claimed in claim 21, wherein the step of adding a drug to the washed mineralized collagen slurry includes adding a drug selected from the group consisting of antibiotics, bone morphogenetic proteins, other bone growth factors, skin growth factors, antiscarring agents and mixtures thereof.

23. The method for producing a substantially homogeneous mineralized collagen membrane as claimed in claim 21, wherein the step of adding a drug to the washed mineralized collagen slurry includes the steps of drying the mineralized collagen membrane, soaking the dried mineralized collagen membrane in a solution of a selected drug, and drying the drug soaked mineralized collagen membrane to incorporate the drug into the mineralized collagen membrane.

24. The method for producing a substantially homogeneous mineralized collagen membrane as claimed in claim 14, including the step of adding a cross-linking reagent into the mineralized collagen slurry before the slurry is formed into a thin sheet.

25. The method for producing a substantially homogeneous mineralized collagen membrane as claimed in claim 14, including the step of soaking the dry mineralized collagen membrane in a collagen cross-linking reagent.

26. The method for producing a substantially homogeneous mineralized collagen membrane as claimed in claim 25, including the step, after the cross-linking process is completed, of soaking and washing the membrane with pure water to remove any un-reacted cross-linking reagent.

27. A method for producing a substantially homogeneous thin mineralized collagen membrane comprising the steps of:
a. forming a collagen slurry;
b. forming a soluble calcium ion-containing solution;
c. forming a soluble phosphate ion containing solution;
d. adding said soluble calcium ion-containing solution and said soluble phosphate ion-containing solution to said collagen slurry while stirring the collagen slurry and maintaining the pH of said collagen slurry in the range of at least about 7, thereby inducing the precipitation of calcium phosphate mineral in the collagen slurry as mineralized collagen slurry, said soluble phosphate ion containing solution being formed so that the mineralized collagen membrane comprises about 10% to about 70% calcium phosphate minerals and about 30% to about 70% collagen;
e. aging the collagen slurry for sufficiently long after the step of adding said soluble calcium ion-containing solution and said soluble phosphate ion-containing solution to said collagen to ensure at least substantially complete precipitation of calcium phosphate;
f. recovering said mineralized collagen slurry by solid-liquid separation;
g. washing the recovered mineralized collagen slurry with pure water;
h. casting the washed mineralized collagen slurry into a thin flat sheet on a filter media; and
i. drying said thin flat sheet and removing it from the filter media as a thin mineralized collagen membrane having a thickness not greater than about 0.3 mm.

28. The method for producing a substantially homogeneous thin mineralized collagen membrane as claimed in claim 27, wherein said soluble calcium ion-containing solution and said soluble phosphate ion containing solution are formed so that said calcium phosphate minerals comprise calcium phosphate, tri-calcium phosphate, octa-calcium phosphate, calcium deficient apatite, amorphous calcium phosphate, hydroxyapatite, substitute apatite, apatite-like minerals, or a mixture thereof.

29. The method for producing a substantially homogeneous mineralized collagen membrane as claimed in claim 27, wherein said step of adding said soluble calcium ion-containing solution and said soluble phosphate ion-containing solution to said collagen slurry while stirring the collagen slurry includes maintaining the pH of said collagen slurry at not less than about 9.

30. The method for producing a substantially homogeneous mineralized collagen membrane as claimed in claim 27, including the step of adding a drug to the washed mineralized collagen slurry, said drug being selected from the group consisting of antibiotics, bone morphogenetic proteins, other bone growth factors, skin growth factors, antiscarring agents and mixtures thereof.

31. A thin mineralized collagen membrane useful for medical applications such guided tissue regeneration for periodontal defect repairs, for covering bone defects, for bone grafts, for soft tissue flaps over bone grafts, for skin wound healing, for skin sealing, for bone substitutes, for a carrier for antibiotics, bone and skin growth factors, and skin and bone repair materials, said mineralized collagen membrane comprising a substantially homogeneous mineralized collagen composite consisting essentially of about 30% to about 70% by weight of a collagen component and about 30% to about 70% by weight of a calcium phosphate minerals component precipitated from a collagen slurry by a soluble calcium ion-containing solution and a soluble phosphate ion-containing solution, and having a bulk density of at least about 1.0 g/cm$^3$ and having a thickness not greater than about 0.5 mm.

32. The thin mineralized collagen membrane as claimed in claim 31, wherein said calcium phosphate minerals component has a mole ratio of calcium to phosphate in the range of about 1.0 to about 2.0.

33. The thin mineralized collagen membrane as claimed in claim 31, wherein said membrane has a thickness not greater than about 0.3 mm.

* * * * *